DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 30, 1971

892 O.G. 1605

T892,024

PROCESS FOR THE ISOMERIZATION OF DIMETHYL CIS-1,4-CYCLOHEXANEDICARBOXYLATE TO THE TRANS-ISOMER

John G. Thweatt, Rte. 11 37663, and Wayne V. McConnell, 1509 Ardmore Place 37664, both of Kingsport, Tenn.

Filed May 13, 1970, Ser. No. 36,997
Int. Cl. C07c *67/00, 69/74*
U.S. Cl. 260—468 R
No Drawing. 6 Pages Specification

A process for isomerizing a mixture of cis- and trans-dimethyl 1,4-cyclohexanedicarboxylate containing a high content of the cis-isomer to mixtures containing much larger amounts of the trans-isomer by heating the original mixture in the presence of an acidic catalyst which is insoluble in the mixture of cis- and trans-isomers. The insoluble catalyst can be removed from the reaction mixture by filtration or decantation, permitting either the substantially pure trans-isomer or at least a mixture of cis- and trans-isomers uncontaminated with the catalyst to be recovered. The ratio of catalyst employed with respect to the cis- and trans-mixture may range from about 0.005 to 1.0. When operating at atmospheric pressure heating may be at a temperature of 200–265° C. Carrying out the reaction at super-atmospheric pressures permits the use of higher temperatures.